United States Patent [19]

Maillard et al.

[11] 4,443,468
[45] Apr. 17, 1984

[54] BENZOFURAN DERIVATIVES, PROCESS FOR THEIR PREPARATION AND THEIR THERAPEUTIC APPLICATIONS

[75] Inventors: J. Georges Maillard, Versailles; Jacky Legeai, Palaiseau, both of France

[73] Assignee: Laboratoires Jacques Logeais, Issy-les Moulineaux, France

[21] Appl. No.: 355,331

[22] Filed: Mar. 5, 1982

Related U.S. Application Data

[62] Division of Ser. No. 54,626, Jul. 3, 1979, Pat. No. 4,339,384.

[30] Foreign Application Priority Data

Jul. 17, 1978 [FR] France .................................. 78 21188

[51] Int. Cl.³ .............................................. A61K 31/40
[52] U.S. Cl. ..................................................... 424/274
[58] Field of Search ........................ 548/525; 424/274

[56] References Cited

FOREIGN PATENT DOCUMENTS 78824 2/1980 France ................................ 424/274
4720019 5/1970 Japan .................................. 424/274

*Primary Examiner*—Paul M. Coughlan, Jr.
*Assistant Examiner*—D. B. Springer
*Attorney, Agent, or Firm*—Young & Thompson

[57] ABSTRACT

This invention relates to compounds having the general formula:

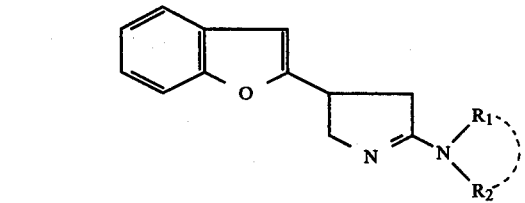

in which

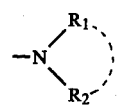

is selected from: a radical

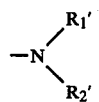

in which $R'_1$ is hydrogen and $R'_2$ is selected from hydrogen; $C_{1-6}$ alkyl; $C_{2-6}$ alkenyl; $C_{2-6}$ alkynyl; phenyl; phenyl $C_{1-6}$ alkyl; mono-, di- and trimethoxyphenyl $C_{1-6}$ alkyl; $C_{1-6}$ alkoxy; benzyloxy; di-$C_{1-6}$ alkylamino-$C_{1-6}$ alkyl; $C_{1-6}$ hydroxyalkyl; $C_{1-6}$ alkyloxycarbonyl-$C_{1-6}$ alkyl; or $R'_1$ and $R'_2$ are joined to form a heterocyclic ring;

and their pharmacologically acceptable inorganic and organic acid addition salts.

Said compounds are therapeutically useful for the treatment of dysrhythmia.

3 Claims, No Drawings

BENZOFURAN DERIVATIVES, PROCESS FOR THEIR PREPARATION AND THEIR THERAPEUTIC APPLICATIONS

This application is a division of application Ser. No. 054,626 filed July 3, 1979 now U.S. Pat. No. 4,339,384.

DESCRIPTION

This invention relates to new benzofuran derivatives, to a process for their preparation and to their therapeutic applications.

This invention relates to compounds having the general formula:

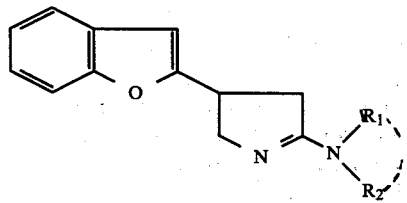

(I)

in which

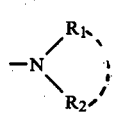

is selected from:
A radical

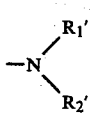

in which $R'_1$ is hydrogen and $R'_2$ is selected from hydrogen; $C_{1-6}$ alkyl; $C_{2-6}$ alkenyl; $C_{2-6}$ alkynyl; phenyl; phenyl $C_{1-6}$ alkyl; mono-, di- and trimethoxyphenyl $C_{1-6}$ alkyl; $C_{1-6}$ alkoxy; benzyloxy; di- $C_{1-6}$ alkylamino-$C_{1-6}$ alkyl; $C_{1-6}$ hydroxyalkyl; $C_{1-6}$ alkyloxycarbonyl-$C_{1-6}$ alkyl;
a radical

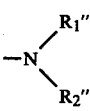

in which $R''_1$ and $R''_2$ are $C_{1-6}$ alkyl;
a radical

in which n is selected from 4, 5
the radical

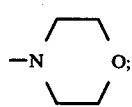

and
the radical

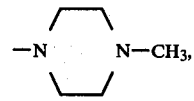

and their pharmacologically acceptable inorganic and organic acid addition salts.

The salts may typically be those formed with hydrochloric, sulfuric, phosphoric, methane-sulfonic, maleic, succinic, pamoic, acetic, fumaric, lactic, aspartic and citric acids.

The compounds of the formula (I) may be prepared according to the following scheme:

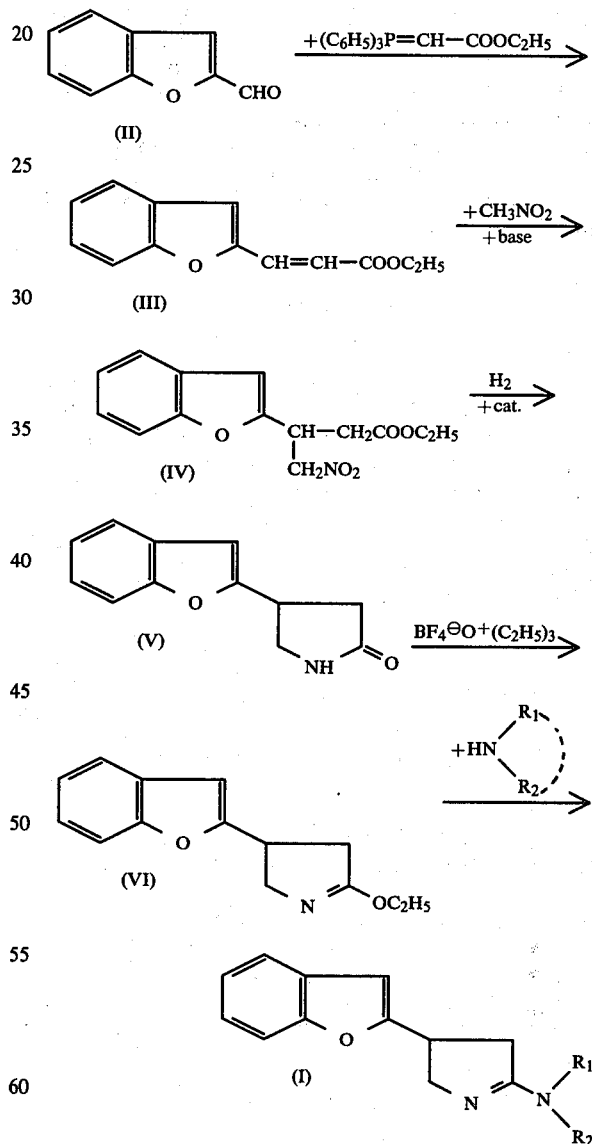

The first reaction comprises reacting 2-formylbenzofuran (Bull. Soc. Chim. France 1962, p. 1875) with carbethoxy-methylidene-triphenyl-phosphoran, under the usual conditions for the conventional Wittig reaction, within an inert solvent such as benzene or toluene.

This reaction provides ethyl 3-(2-benzofuryl)acrylate (III) which has already been disclosed by Foo Pan and Tsan Ching Wang (J. Chinese Chem. Soc. 1961, series II, 8, 374–9).

The resulting acrylate (III) is then reacted with nitromethane (generally used as solvent for the reaction) in the presence of a strong base such as Triton B (benzyltrimethylammonium hydroxide) or of a metal alkoxide such as sodium ethoxide or methoxide, to give the nitro ester (IV). The reaction may also be effected in another solvent such as dimethylformamide.

The nitro ester (IV) is reduced by hydrogenation, at ordinary pressure in the presence of a catalyst such as Raney nickel within a solvent such as ethanol: the intermediately formed amino-ester is cyclized by heating to pyrrolidin-2-one (V).

Pyrrolidinone (V) is treated with triethyloxonium tetrafluoroborate within an inert solvent such as methylene chloride and converted to 2-ethoxy-pyrroline (VI).

The latter is reacted with an amine $HNR_1R_2$ within a solvent such as ethanol, to give 2-amino-pyrroline (I), which, if desired, is then converted to a salt according to the usual procedures. In the case of volatile amines, these may be used as the hydrochlorides, to give directly the hydrochlorides of 2-amino-pyrrolines (I).

The following non-limiting Examples are given to illustrate the present invention.

EXAMPLE 1

(I) $R_1 = R_2 = H$ (a) Ethyl 3-(2-benzofuryl)acrylate (III)

A mixture of 35 g (0.24 mole) 2-formyl-benzofuran (II) and 83.5 g (0.24 mole) carbethoxymethylidene-triphenylphosphoran in 300 ml benzene is refluxed under a nitrogen atmosphere for 7 hours. After evaporation to dryness, under reduced pressure, the residue is triturated with ether, suction filtered, and recrystallized from isopropyl ether.

M.p. (inst.) = 78° C. Yield: 100%.

The resulting product may contain some triphenylphosphine oxide formed in the course of the reaction. It may be stripped therefrom by distillation (B.p.$_{0.2}$ = 126° C. or B.p.$_{0.5}$ = 140° C. (Yield = 80%).

(b) Ethyl 4-nitro-3-(2-benzofuryl)butyrate (IV)

51.8 g (0.24 mole) of derivative (III) obtained in (a) above, 61 g (1 mole) nitromethane and 10 ml Triton B (40% solution in methanol) are heated to 70°–90° C. for 16–24 hours. After cooling and slow acidification with normal hydrochloric acid, the nitro ester is extracted with ether, washed with water, dried over anhydrous sodium sulfate. Evaporation of the ether leaves an oily nitroester residue which is purified by flash distillation. B.P.$_{0.1}$ = 150° C. or B.P.$_{0.6}$ = 178° C.

The head fractions containing unreacted ester (III) may be recycled to another operation (Average yield for 3 successive operations: 69%).

(c) 4-(2-Benzofuryl)pyrrolidin-2-one (V)

Ester (IV) (81.5 g; 0.297 mole) obtained in b) is dissolved in 500 ml ethanol and hydrogenated at ordinary pressure at 55° C. in the presence of 10 g Raney Nickel. The hydrogen required for the reaction (14.8 l) is taken up within 7 hours. After filtration of the catalyst and evaporation of the ethanol, the oily residue is heated at 100° C. under the vacuum of a water pump, for 2 hours. On trituration with isopropyl ether, the product crystallizes. M.P. (inst.) = 142° C. Weight: 47.9 g (80%).

(d) 2-Ethoxy-4-(2-benzofuryl)Δ-1-pyrroline (VI)

8 g (0.04 mole) 4-(2-benzofuryl)pyrrolidin-2-one (V) and 12 g (0.06 mole) triethyloxonium tetrafluoroborate are dissolved in 80 ml methylene chloride and stirred for a period of time of one week at ordinary temperature. The mixture is then hydrolyzed by addition of 15 g potassium hydroxide dissolved in 30 ml water. The insoluble is filtered off and the organic phase is washed with water, dried over sodium sulfate, and distilled. B.p.$_{0.3}$ = 128°–130° C. Weight: 5.9 g (64%).

(e) 2-Amino-4-(2-benzofuryl)Δ-1-pyrroline hydrochloride

The 5.9 g (0.025 mole) of derivative (VI) obtained in the preceding reaction are dissolved in 50 ml ethanol, with 1.36 g (0.025 mole) ammonium chloride. The desired hydrochloride of the amino derivative crystallizes on cooling. It is suction filtered and dried in vacuo. M.p. (inst.) = 253° C. Weight: 4 g (42%).

EXAMPLE 2

(I) $R_1 = H$; $R_2 = CH_3$

2-Methylamino-4-(2-benzofuryl)Δ-1-pyrroline hydrochloride

The above compound is obtained in the same manner as the derivative (I) of Example 1, by action of methylamine hydrochloride on 2-ethoxy-4-(2-benzofuryl)Δ-1-pyrroline (VI), within boiling ethanol. The solution is then evaporated to dryness and the residue is taken up into hot ethanol. After addition of ethyl acetate and stirring for 24 hours at ordinary temperature, the precipitate is suction filtered and dried. M.p. (inst.) = 151° C. Yield: 45%.

EXAMPLE 3

(I) $R_1 = H$; $R_2 = iC_3H_7$

2-Isopropylamino-4-(2-benzofuryl)Δ-1-pyrroline hydrochloride

The above compound is obtained in the same manner as the derivative (I) of Example 1, by action of isopropylamine hydrochloride on derivative (VI) within boiling ethanol. After evaporation of the solvent, the residue is taken up into hot isopropanol: the desired hydrochloride crystallizes on addition of isopropyl ether followed by cooling.

M.p.(inst.) = 186° C. Yield: 66%.

EXAMPLE 4

(I) $R_1 = R_2 = CH_3$

2-Dimethylamino-4-(2-benzofuryl)Δ-1-pyrroline hydrochloride

The above compound is obtained in the same manner as the derivative (I) of Example 1, by action of dimethylamine hydrochloride on 2-ethoxy-4-(2-benzofuryl)Δ-1-pyrroline (VI) within hot ethanol. After evaporation to dryness and taking up with isopropanol, the hydrochloride crystallizes on addition of ether.

M.p. (inst.) = 154° C. Yield: 84%.

EXAMPLE 5

(I) $R_1=R_2=C_2H_5$

2-Diethylamino-4-(2-benzofuryl)Δ-1-pyrroline fumarate

The hydrochloride is obtained by the procedure of the preceding Examples, by action of diethylamine hydrochloride on derivative (VI), within boiling ethanol (20 hrs). After evaporation of the solvent, the residue is taken up into chloroform, after which the solution is washed with N sodium hydroxide and then with water. The oily residue remaining after evaporation of the chloroform is distilled under reduced pressure.

B.p.$_{0.1}$=162°-168° C.

The resulting base is dissolved in propanol, with the stoichiometric amount of fumaric acid, in the hot. The fumarate crystallizes on cooling.

M.p.(inst.)=154° C. Yield: 35%.

EXAMPLE 6

(I) $R_1=H$; $R_2=C_6H_5$

2-Anilino-4-(2-benzofuryl)Δ-1-pyrroline hydrochloride

The base is prepared by action of excess aniline on derivative (VI), within refluxing ethanol (48 hrs). After evaporation under reduced pressure, the residue is taken up into ethyl acetate, within which the base crystallizes on stirring.

The above base is converted to the hydrochloride by addition of a solution of anhydrous HCl in ethanol to a solution of the base in isopropanol, in the hot. The hydrochloride crystallizes on cooling.

M.p.(inst.)=203° C. Yield: 58%.

EXAMPLE 7

(I) $R_1=H$; $R_2=CH_2CH_2C_6H_5$

2-Phenethylamino-4-(2-benzofuryl)Δ-1-pyrroline hydrochloride

The base is obtained as that of the derivative of Example 6, from phenethylamine within ethanol, and is then converted to the hydrochloride, M.p.(inst.)=121° C. Yield=62%.

EXAMPLE 8

(I) $R_1-R_2=-(CH_2)_4-$

2-Pyrrolidino-4-(2-benzofuryl)Δ-1-pyrroline hydrochloride

The above compound is obtained in the same manner as the derivative (I) of Example 1, by action of pyrrolidine hydrochloride on derivative (VI), within hot ethanol. After evaporation of the solvent and re-dissolution in hot isopropanol, the hydrochloride crystallizes on addition of isopropyl ether and cooling.

M.p.(inst.)=260° C. Yield: 84%.

EXAMPLE 9

(I) $R_1-R_2=-(CH_2)_2-O-(CH_2)_2-$

2-Morpholino-4-(2-benzofuryl)Δ-1-pyrroline hydrochloride

The above compound is obtained in the same manner as the derivative (I) of Example 1, by action of morpholine hydrochloride on derivative (VI) within hot ethanol, followed by recrystallization from isopropanol.

M.p.(inst.)=195° C. Yield:81%.

EXAMPLE 10

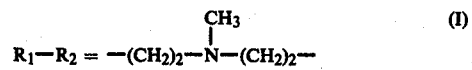

2-(4-Methyl-piperazino)-4-(2-benzofuryl)Δ-1-pyrroline methanesulfonate

The above compound is obtained in the same manner as the derivative (I) of Example 1, by action of N-methylpiperazine on derivative (VI) within ethanol, in the hot. After evaporation under reduced pressure, the residue is triturated with petroleum ether, suction filtered and dried. M.p.(inst.)=124.5° C. Yield=58%.

The base is converted to the methanesulfonate by addition of a slight deficiency of methanesulfonic acid, within ethyl acetate, and stirring for 3 hrs. The insoluble salt is suction filtered and dried. M.p. 146° C. Yield: 79.5%.

EXAMPLE 11

(I) $R_1=H$; $R_2=CH_2CH_2N(CH_3)_2$ 2-(2-Dimethylamino-ethyl)-4-(2-benzofuryl)Δ-1-pyrroline dihydrochloride The above compound is obtained in the same manner as the derivative of Example 6, by action of 2-dimethylamino ethylamine on derivative (VI), in the hot, within ethanol, followed by conversion of the base to the dihydrochloride, within isopropanol. The dihydrochloride crystallizes on cooling. M.p.(inst.): 240° C. Yield: 52%.

EXAMPLE 12

(I) $R_1=H$; $R_2=OC_2H_2C_6H_5$

2-Benzyloxyamino-4-(2-benzofuryl)Δ-1-pyrroline hydrochloride

The above compound is obtained in the same manner as the derivative (I) of Example 1, by action of benzyloxyamine hydrochloride on derivative (VI) within ethanol, in the hot. After evaporation of the solvent and re-dissolution in hot isopropanol, the hydrochloride crystallizes on addition of isopropyl ether and cooling.

M.p.(inst.)=183° C. Yield: 39%.

EXAMPLE 13

(I) $R_1=H$; $R_2=OCH_3$

2-Methoxyamino-4-(2-benzofuryl)Δ-1-pyrroline hydrochloride

The above compound is obtained in the same manner as the derivative (I) of Example 1, by action of O-methylhydroxylamine hydrochloride on derivative (VI) within hot ethanol. M.p.(inst.)=184° C. (with dec.). Yield=67%.

EXAMPLE 14

(I) $R_1=H$; $R_2=CH_2CH=CH_2$

2-Allylamino-4-(2-benzofuryl)Δ-1-pyrroline hydrochloride

The above compound is obtained in the same manner as the derivative (I) of Example 6, by action of allylamine on compound (VI), within hot ethanol. After evaporation to dryness, the residue is converted to the hydrochloride by addition of a solution of HCl in anhydrous ether. M.p.=160° C. Yield=98%.

EXAMPLE 15

(I) $R_1=H$; $R_2=CH_2C\equiv CH$

2-Propargylamino-4-(2-benzofuryl)Δ-1-pyrroline hydrochloride

The above compound is obtained in the same manner as the derivative (I) of Example 1, by action of propargylamine hydrochloride on compound (VI), within hot ethanol. After evaporation of the solvent, the residue is recrystallized from isopropanol. M.p.=196° C. Yield: 75%.

EXAMPLE 16

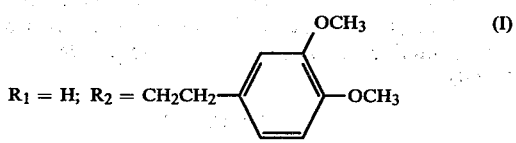

$R_1=H$; $R_2=CH_2CH_2$— (I)

2-(3,4-Dimethoxy-phenethylamino)-4-(2-benzofuryl)Δ-1-pyrroline hydrochloride

The above compound is obtained in the same manner as the derivative (I) of Example 1, by action of 2-(3,4-dimethoxy-phenyl)ethylamine hydrochloride on compound (VI) within hot ethanol. After evaporation of the solvent, the residue is recrystallized from isopropanol. M.p.=180° C. Yield: 76%.

EXAMPLE 17

(I) $R_1=H$; $R_2=CH_2CH_2OH$ 2-(2-Hydroxy-ethylamino)-4-(2-benzofuryl)Δ-1-pyrroline hydrochloride The above compound is obtained in the same manner as the derivative (I) of Example 6, by action of ethanolamine on compound (VI) within hot ethanol. The base isolated after evaporation of the ethanol (M.p.=130° C. Yield: 69%) is converted to the hydrochloride with a solution of HCl in anhydrous ether. M.p.=171° C. Yield: 82%.

EXAMPLE 18

(I) $R_1=H$; $R_2=CH_2COOC_2H_5$ 2-(2-Ethoxycarbonyl-ethylamino)-4-(2-benzofuryl)Δ-1-pyrroline hydrochloride The above compound is obtained in the same manner as the derivative (I) of Example 1, by action of ethyl 2-amino-acetate hydrochloride on compound (VI), within hot ethanol. M.p.=168° C. Yield=69%.

The compounds of the formula (I) exhibit useful pharmacological properties, particularly in the cardiovascular field: increase of the arterial rate of flow and antidysrhythmic action. Their toxicity appears only at dosages greatly in excess of the pharmacologically active dosages, which permits their therapeutic use as drugs for the treatment of dysrhythmias aand the improvement of blood circulation.

Results of toxicological and pharmacological investigations which demonstrate said properties are reported below.

(a) Acute toxicity in mice

Each compound was administered orally, intraperitoneally, or intravenously as a single dose. The behavior of the animals and the death rate were observed for several hours after the treatment, and then daily for at least one week. The results obtained are given in Table I below.

TABLE I

| Example | $LD_{50}$, p.o. | $LD_{50}$, i.p. | $LD_{50}$, i.v. | Remarks |
|---|---|---|---|---|
| 1 | 115 mg/kg | 58 mg/kg | 46 mg/kg | Vasodilation |
| 2 | >200 mg/kg | 58 mg/kg | | agitation-convulsions |
| 3 | 200 mg/kg | 58 mg/kg | | convulsions dyspnea |
| 4 | 240 mg/kg | | 38.5 mg/kg | convulsions |
| 5 | 180 mg/kg | 58 mg/kg | | central stimulation |
| 6 | 110 mg/kg | 58 mg/kg | | Hyperesthesia |
| 7 | >200 mg/kg | 98 mg/kg | | Convulsions |
| 8 | 200 mg/kg | 76 mg/kg | | Agitation-convulsions |
| 9 | >200 mg/kg | 142 mg/kg | | Convulsions-cyanosis |
| 10 | >200 mg/kg | 142 mg/kg | | Agitation-convulsions |

(b) Actions on the central nervous system

The central effects of the various compounds were investigated in mice by means of a set of tests:
traction test;
interaction with the hypnotic effect of barbiturates;
oxotremorine test;
reserpine test (ptosis).

The above set of tests failed to evidence a significant effect on the central nervous system.

(c) Cardiovascular effects

The cardiovascular effects of each compound were investigated in anesthetized dogs.

A potent arterial dilator effect was evidenced with a number of compounds.

(d) Anti-dysrhythmic effects

The anti-dysrhythmic activity of the compounds of the formula (I) was evaluated according to the following pharmacological tests:
maximum stimulation heart rate (FMS)

The FMS, as determined in vivo in rabbits by cardiac stimulation by means of a stimulation probe placed in the left auricular cavity, provides an overall determination of the duration of the refractory period of the conductive routes and of the fibres of the myocardium.

dysrhythmia on central stimulation in rabbits: electric stimulation of the posterior hypothalamus induces an intense activation of the sympathetic system and of the dysrhythmias;

aconitine induced dysrhythmias in rats: this agent has a deeply perturbating effect on the ionic permeability of the membranes;

ouabaine induced dysrhythmias in guinea-pigs: at toxic dosages, ouabaine affects transmembrane ionic exchanges; on the other hand, it induces a concomitant sympathetic activation.

anoxia induced dysrhythmias in rats, after pre-treatment with a subliminal dosage of aconitine (combination of the effects of a sympathetic stimulation with those due to perturbations of ionic conductions);

method according to Harris, in dogs: coronary ligation and dysrhythmias induced by localized ischemia.

The results obtained are tabulated in Table II. This Table provides evidence of the potent anti-arhythmic activity of the compounds of the formula (I).

The compounds of the formula (I) are of high therapeutic value in the treatment of a variety of circulatory or cardiac diseases (circulatory insufficiency; vascular obturation; angina pectoris; dysrhythmia, and the like).

The compounds are administrable to humans by the oral or rectal route, as bases or salts (formulated as tablets, capsules, drops or suppositories) or by the parenteral route, as aqueous solutions of water-soluble salts or within another excipient insuring delayed resorption.

The various formulations may contain 10–1000 mg active ingredient per unit dosage for administration by the oral and rectal routes, and 5–500 mg active ingredient for the other routes of administration.

The daily dosage regimen may vary from 10 mg to 3 g, depending on the route of administration and the therapeutic applications contemplated.

amount of a compound selected from the group consisting of compounds having the formula:

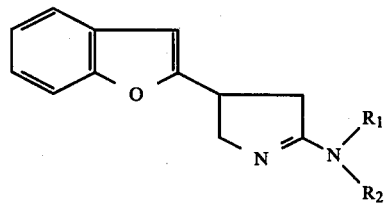

wherein $R_1$ and $R_2$ are $C_{1-6}$ alkyl groups, and a pharmacologically acceptable acid addition salt thereof, and a therapeutically acceptable excipient.

2. A therapeutic composition having anti-dysrhythmic activity as claimed in claim 1, wherein $R_1$ and $R_2$ are methyl groups.

3. A therapeutic composition having an anti-dysrhythmic activity containing an anti-dysrhythmic effective amount of a compound selected from the group consisting of:

2-methylamino-4-(2-benzofuryl)Δ-1-pyrroline,
2-isopropylamino-4-(2-benzofuryl)Δ-1-pyrroline,
2-dimethylamino-4-(2-benzofuryl)Δ-1-pyrroline,

TABLE II

| Example N° | FMS Rabbit | Central stimulation Rabbit | Antidysrhythmic Activity Aconitine Rat | Anoxia Rat | Ouabaine Cobaye | Harris Ligation Dog |
|---|---|---|---|---|---|---|
| 2 | + (7.5 mg/kg) | + (3 mg/kg) | + (10 mg/kg) | | | |
| 3 | | | 0 | + (10 mg/kg) | | |
| 4 | + (2.5 mg/kg) | ++ (5 mg/kg) | ++ (10–20 mg/kg) | ++ (10–20 mg/kg) | + (10–20 mg/kg) | + (10 mg/kg) |
| 5 | | | ++ 10–20 mg/kg | | | |
| 6 | + (2.5 mg/kg) | + (2.5 mg/kg) | | 0 | | |
| 7 | + (2 mg/kg) | 0 | + (5 mg/kg) | | | |
| 8 | | | + (10 mg/kg) | + (10 mg/kg) | | |
| 9 | | | ± (10 mg/kg) | 0 | | |
| 10 | | | 0 | + (10 mg/kg) | | | i.v. dosage
0: no effect
+: moderate action
++: marked action.

Having now described our invention what we claim as new and desire to secure by Letters Patent is:

1. A therapeutic composition having an antidysrhythmic activity containing an anti-dysrhythmic effective 2-diethylamino-4-(2-benzofuryl)Δ-1-pyrroline,
2-anilino-4-(2-benzofuryl)Δ-1-pyrroline,
2-phenethylamino-4-(2-benzofuryl)Δ-1-pyrroline,
2-pyrrolidino-4-(2-benzofuryl)Δ-1-pyrroline,
and a pharmacologically acceptable acid addition salt thereof, and a therapeutically acceptable excipient.

* * * * *